(12) United States Patent
Endoh et al.

(10) Patent No.: US 7,897,814 B2
(45) Date of Patent: Mar. 1, 2011

(54) METHOD FOR EXTRACTING METHACRYLIC ACID

(75) Inventors: Tohru Endoh, Hatsukaichi (JP); Kazunori Matake, Otake (JP); Shigeho Tanaka, Otake (JP); Haruki Sato, Hatsukaichi (JP)

(73) Assignee: Mitsubishi Rayon Co., Ltd., Tokyo (JP)

( * ) Notice: Subject to any disclaimer, the term of this patent is extended or adjusted under 35 U.S.C. 154(b) by 307 days.

(21) Appl. No.: 12/159,318

(22) PCT Filed: Dec. 26, 2006

(86) PCT No.: PCT/JP2006/325926

§ 371 (c)(1),
(2), (4) Date: Oct. 16, 2008

(87) PCT Pub. No.: WO2007/074827

PCT Pub. Date: Jul. 5, 2007

(65) Prior Publication Data

US 2010/0228053 A1  Sep. 9, 2010

(30) Foreign Application Priority Data

Dec. 26, 2005  (JP) .............................. 2005-371337

(51) Int. Cl.
*C07C 51/42* (2006.01)

(52) U.S. Cl. ...................................................... 562/600
(58) Field of Classification Search ....................... None
See application file for complete search history.

(56) References Cited

U.S. PATENT DOCUMENTS 3,962,074 A  6/1976  Schropp

FOREIGN PATENT DOCUMENTS

| EP | 0 271 371 | 6/1988 |
|---|---|---|
| JP | 50-18412 | 2/1975 |
| JP | 52-153909 | 12/1977 |
| JP | 62-120341 | 6/1987 |
| JP | 63-135350 | 6/1988 |
| JP | 63-211249 | 9/1988 |
| JP | 7-118198 | 5/1995 |
| JP | 3246216 | 5/1995 |
| JP | 07118198 A * | 5/1995 |
| JP | 2001-514643 | 9/2001 |

* cited by examiner

*Primary Examiner*—Paul A Zucker
(74) *Attorney, Agent, or Firm*—Oblon, Spivak, McClelland, Maier & Neustadt, L.L.P.

(57) ABSTRACT

Disclosed is a method for extracting methacrylic acid, in which an extraction solvent is added to a methacrylic acid aqueous solution for transferring methacrylic acid to the extraction solvent. In this method, a solvent containing t-butyl methacrylate is used as the extraction solvent.

4 Claims, No Drawings

METHOD FOR EXTRACTING METHACRYLIC ACID

TECHNICAL FIELD

The present invention relates to a method for extracting methacrylic acid from a methacrylic acid aqueous solution.

The present application claims the priority of Japanese Patent Application No. 2005-371337 filed on Dec. 26, 2005, the contents of which are incorporated herein by reference.

BACKGROUND ART

At the time of purifying methacrylic acid by separating water from a methacrylic acid aqueous solution, a method has been widely known in which methacrylic acid is extracted from the methacrylic acid aqueous solution by an extraction solvent and then methacrylic acid is separated from the extraction solvent. As the extraction solvent to be used in the extraction of methacrylic acid, for example, at least one extracting agent, which can be converted into (meth)acrylic acid, selected from the group consisting of an alkane, alkanol, alkene, and alkenal each having 3 to 4 carbon atoms and methyl tertiary butyl ether (MTBE) is disclosed in Patent Document 1.

Methyl methacrylate or a mixed solvent of methyl methacrylate and n-heptane is disclosed in Patent Document 2.

A mixed solvent containing an aromatic hydrocarbon selected from the group consisting of benzene, toluene, and xylene; and an aliphatic hydrocarbon selected from the group consisting of n-hexane, n-heptane, and n-octane, in which the content of the aromatic hydrocarbon is 20 to 70% by mass, is disclosed in Patent Document 3.

Patent Document 1: Published Japanese Translation No. 2001-514643 of the PCT International Publication Patent Document 2: Japanese Patent No. 3246216

Patent Document 3: Japanese Patent Application Laid-Open No. 63-211249

DISCLOSURE OF INVENTION

Problem to be Solved by the Invention

However, the extraction solvent disclosed in Patent Document 1 has insufficient ability of extracting methacrylic acid and hence its extraction efficiency is low, so that a large quantity of the extraction solvent has been necessarily used. Further, the extraction solvent disclosed in Patent Document 1 has a high solubility to water and a large part of the extraction solvent is transferred to the water phase, so that it takes much time to recover the extraction solvent from the water phase or the load of wastewater treatment is increased because the extraction solvent is discharged together with the wastewater, and hence the extraction solvent has been uneconomical.

There is little difference in specific gravities between methyl methacrylate disclosed in Patent Document 2 and water, and there has been a problem of separability. Further, a large quantity of the extraction solvent has necessarily been used because n-heptane as the extraction solvent has insufficient ability of extracting methacrylic acid and hence its extraction efficiency is low in the mixed solvent of n-heptane and methyl methacrylate.

The mixed solvent disclosed in Patent Document 3 includes aliphatic hydrocarbons represented by n-heptane, and hence a large quantity of the extraction solvent has necessarily been used because its ability of extracting methacrylic acid is low.

After methacrylic acid is extracted using an extraction solvent, usually, separation of methacrylic acid from the extraction solvent is carried out. As the separation method, distillation method is widely applied in view of simplicity of operation and equipment.

The distillation method is usually carried out under reduced pressure because it is necessary to keep the distillation temperature low in order to inhibit the polymerization of methacrylic acid. However, the extraction solvents disclosed in the patent documents 1 to 3 have low boiling points and differences of boiling points between these extraction solvents and methacrylic acid are large, so that there has been a case that a condensation temperature becomes low under reduced pressure. When the condensation temperature becomes low, it is uneconomical because a specific coolant is needed to carry out condensation.

The present invention has been completed in view of the above-mentioned circumstances, and it is an object of the present invention to provide a method for extracting methacrylic acid which has the high extraction efficiency for methacrylic acid and is economical.

Means for Solving the Problem

The present inventors have diligently researched an extraction solvent having a high ability of extracting methacrylic acid in order to solve the above-mentioned problem and thus have invented the following method for extracting methacrylic acid.

Namely, the present invention is a method for extracting methacrylic acid, comprising the steps of:

(a) adding an extraction solvent comprising t-butyl methacrylate to a methacrylic acid aqueous solution; and (b) causing methacrylic acid to transfer to the extraction solvent.

Effect of the Invention

According to the method for extracting methacrylic acid of the present invention, the extraction efficiency for methacrylic acid is high, and moreover, the method is economical.

Best Mode for Carrying Out the Invention

The extraction method of the present invention is not particularly limited as long as the desired quantity of methacrylic acid can be recovered. As an operation of extraction, any one of a continuous extraction, continuous multistage extraction, single batch extraction, and multiple batch extraction or a combination of them may be carried out. Among them, the continuous multistage extraction is preferable. A flow direction of a liquid in the continuous extraction is not particularly limited, and countercurrent or concurrent can be used. Especially, countercurrent is preferable from the viewpoint of extraction efficiency.

As the methacrylic acid aqueous solution to be used in the method for extracting methacrylic acid of the present invention, though it is not particularly limited, an aqueous solution obtained by synthesizing methacrylic acid through gas-phase or liquid-phase oxidation of isobutylene, t-butanol, or methacrolein with molecular oxygen is exemplified.

The content of methacrylic acid contained in the methacrylic acid aqueous solution is preferably 10 to 90% by mass.

A compound other than methacrylic acid and water may be contained in the aqueous methacrylic acid. For example, impurities originated from the synthesis of methacrylic acid may be contained. As the impurities produced in the gas-phase or liquid-phase oxidation of isobutylene, t-butanol, or methacrolein, for example, isobutylene, t-butanol, acrolein, methacrolein, acetone, acetic acid, acrylic acid, and methacrylic anhydride are listed.

As an extraction solvent to be used in the present invention, an extraction solvent including t-butyl methacrylate is used. It is possible to obtain t-butyl methacrylate from, for example, an addition reaction of isobutylene and methacrylic acid or an esterification reaction of t-butanol and methacrylic acid.

The purity of t-butyl methacrylate to be used in the production of the solvent is not particularly limited, however, the higher the purity is better for minimizing the effect of unexpected impurities.

The extraction solvent may be t-butyl methacrylate alone or one containing another additional solvent. As the other solvent, for example, hydrocarbons, aromatic hydrocarbons, esters, ketones, or alcohols are listed, and it can be properly selected in accordance with availability or budget. Among these solvents, esters are preferable and methyl methacrylate is more preferable because it has a high extraction ability of methacrylic acid and its solubility to water is low, and moreover there is a large difference in specific gravity between it and water. Namely, as the extraction solvent, a mixture of t-butyl methacrylate and methyl methacrylate is preferable.

In the case that the extraction solvent is a mixture containing t-butyl methacrylate and methyl methacrylate, the mixing ratio of them is not particularly limited. Methyl methacrylate and t-butyl methacrylate can be mixed in any ratio because the mutual solubility of t-butyl methacrylate and methyl methacrylate is high. The extraction efficiency of the mixture for methacrylic acid increases as the mixing ratio of methyl methacrylate becomes higher, though separability of the mixture from water phase tends to become low.

Consequently, as the mixing ratio, the mass fraction of methyl methacrylate is preferably 3 to 90% with respect to 100% by mass of the mixture of t-butyl methacrylate and methyl methacrylate, and more preferably, 10 to 80%.

In the case that the extraction solvent contains another solvent other than methyl methacrylate, the mass fraction of the other solvent is preferably 3 to 90% with respect to 100% by mass of the mixture of t-butyl methacrylate and the other solvent.

The extraction amount of methacrylic acid from the methacrylic acid aqueous solution can be controlled by extraction conditions such as an extraction temperature, an extraction pressure, and an extractor, and the amount of an extraction solvent to be used.

As the extraction temperature becomes lower, the extraction efficiency for methacrylic acid is more improved. However, as the extraction temperature becomes lower, the amount of energy for cooling increases, so that the temperature is preferably in the range of 0 to 60° C. as the extraction temperature. The extraction pressure may be any one of an atmospheric pressure, elevated pressure, and reduced pressure, especially, the atmospheric pressure is preferable because a simple extractor and an easy extraction operation can be adopted.

As the extractor, for example, a mixer-settler extractor, rotating disk extraction column, or perforated-tray extraction column can be used.

The amount of the extraction solvent to be used is preferably in the range of 0.5 to 15 times with respect to the total mass of the methacrylic acid aqueous solution. When the amount of the extraction solvent to be used is 0.5 times or more with respect to the total mass of the methacrylic acid aqueous solution, the amount of extraction of methacrylic acid is increased, and when the amount of the extraction solvent to be used is 15 times or less, the amount of energy needed for the separation of methacrylic acid from the extraction solvent is decreased.

In the case that a solid is deposited when the extraction solvent is added to the methacrylic acid aqueous solution, it is preferable to previously bring the methacrylic acid aqueous solution into contact with the extraction solvent to deposit the solid, and to separate the deposited solid by a solid-liquid separation means such as filtration and separation, and then to introduce only the liquid component into an extractor.

The method for extracting methacrylic acid as explained above has a high ability of extracting methacrylic acid and is excellent in the extraction efficiency for methacrylic acid because t-butyl methacrylate is contained in the extraction solvent. Further, the method is economical because it does not take much time and energy for recovering the extraction solvent from water phase since t-butyl methacrylate has low solubility to water, there is a large difference in specific gravity between t-butyl methacrylate and water, and hence t-butyl methacrylate is excellent in separability from water phase.

After methacrylic acid has been transferred to the extraction solvent by the above-mentioned method, methacrylic acid is separated from the extraction solvent and purified to obtain methacrylic acid having a high purity. As the method for separating methacrylic acid from the extraction solvent, though it is not particularly limited, separation by distillation is preferable because it is economical and easy, and in particular, separation by distillation under reduced pressure is more preferable from the viewpoint of inhibiting polymerization.

As the distillation apparatus for carrying out separation by distillation, though it is not particularly limited, a plate column, a packed column, or the like can be used.

The distillation temperature is not particularly limited, however, it is preferably 50 to 120° C. as the temperature at the bottom of the distillation column, and more preferably 70 to 100° C. from the viewpoint of retarding polymerization of methacrylic acid and t-butyl methacrylate. It is preferable that the distillation pressure be properly controlled to a certain reduced pressure to attain the above-mentioned preferable temperature range.

In the present invention, when the distillation under reduced pressure is applied to separate methacrylic acid from the extraction solvent by distillation, the condensation temperature of the vapor to be obtained from the column top cannot become low easily because t-butyl methacrylate is used as the extraction solvent, which has a high boiling point and there is little difference in boiling point between t-butyl methacrylate and methacrylic acid. Consequently, it is possible to cool the vapor by cold water and the like, and hence it does not need to use any special cooling media for condensation so that this is economical.

As a solvent having a high boiling point other than t-butyl methacrylate, for example, each xylene can be listed as shown in Table 1. However, separability of each xylene from methacrylic acid is low and their perfect separation is difficult. Therefore, recovery efficiency of methacrylic acid is lowered. Then, methacrylic acid that has not been separated from the xylene is sent to an extraction step together with the xylene. On the other hand, t-butyl methacrylate has excellent separability to methacrylic acid, and hence recovery efficiency of methacrylic acid is high.

With respect to volatile organic solvents such as xylene, harmful influence on the human body has been reported. It is possible that these volatile organic solvents will be restricted for use from the viewpoint of securing safety because there is a possibility of their diffusion into the atmosphere at the time of their use or their entrainment into products owing to their insufficient separation. For example, Ministry of Health, Labour and Welfare of Japan has determined a guideline value of xylene concentration in the air inside a room as 0.2 ppm. According to the method of the present invention, these materials are not used and a high extraction rate of methacrylic acid can be obtained.

TABLE 1

| Solvent | Boiling point (° C.) |
| --- | --- |
| Methacrylic acid | 161.0 |
| Methyl methacrylate | 100.3 |
| Benzene | 80.1 |
| Toluene | 110.6 |
| o-xylene | 144.4 |
| p-xylene | 138.4 |
| m-xylene | 139.1 |
| n-hexane | 68.7 |
| n-heptane | 98.4 |
| n-octane | 125.7 |
| Methyl tertiary butyl ether | 55.2 |
| t-butyl methacrylate | 134.4 |

EXAMPLES

Hereinafter, the present invention will be explained in detail by using Examples and Comparative Examples, however, the present invention is not limited to these Examples.

In the Examples and Comparative Examples, quantitative analysis of methacrylic acid and extraction solvents were carried out with gas chromatography, and quantitative analysis of water was carried out with Karl Fischer moisture meter.

Extraction efficiency for methacrylic acid (MAA) and concentration of extraction solvent in water phase are obtained from the following equations.

Extraction efficiency for MAA[%]=Mass of MAA in an upper layer [g]/Mass of MAA charged [g]×100

Concentration of extraction solvent in water phase[%]=Mass of the extraction solvent in water phase [g]/Total mass of water phase [g]×100

Example 1

To about 70 g of a methacrylic acid aqueous solution (methacrylic acid of 19.8% by mass, water of 80.2% by mass), about 30 g of an extraction solvent composed of 100% by mass of t-butyl methacrylate was added and the resultant mixture was stirred for 1 hour at a room temperature to extract methacrylic acid. After the resultant extract was left to stand for 5 hours, samples were taken from each of an upper layer which is the extraction solvent layer and a lower layer which is water layer, and the extraction efficiency for MAA and the concentration of the extraction solvent in water phase were measured. The results are shown in Table 2.

TABLE 2

| | | Example 1 | Example 2 |
| --- | --- | --- | --- |
| Extraction solvent | | TBMA | TBMA + MMA (TBMA of 66.2% by mass) |
| Amount charged at the time of extraction | Aqueous MAA solution (g) | 70.02 | 70.02 |
| | Extraction solvent (g) | 30.01 | 30.25 |
| Extraction efficiency for MAA (%) | | 78.8 | 82.4 |
| Concentration of extraction solvent in water phase (%) | | 0.1 | 0.5 |

In Table 2, TBMA represents t-butyl methacrylate and MMA represents methyl methacrylate, respectively.

Example 2

The same procedures as in Example 1 were carried out except that an extraction solvent composed of 66.2% by mass of t-butyl methacrylate and 33.8% by mass of methyl methacrylate was used instead of 100% by mass of t-butyl methacrylate to extract methacrylic acid. The extraction efficiency for MAA and the concentration of the extraction solvent in water phase were measured in the same manner as in Example 1. The results are shown in Table 2.

Comparative Example 1

The same procedures as in Example 1 were carried out except that an extraction solvent composed of 100% by mass of heptane was used instead of 100% by mass of t-butyl methacrylate to extract methacrylic acid. The extraction efficiency for MAA and the concentration of the extraction solvent in water phase were measured in the same manner as in Example 1. The results are shown in Table 3.

Comparative Example 2

The same procedures as in Example 1 were carried out except that an extraction solvent composed of 100% by mass of methacrolein was used instead of 100% by mass of t-butyl methacrylate to extract methacrylic acid. The extraction efficiency for MAA and the concentration of the extraction solvent in water phase were measured in the same manner as in Example 1. The results are shown in Table 3.

Comparative Example 3

The same procedures as in Example 1 were carried out except that an extraction solvent composed of 66.6% by mass of heptane and 33.4% by mass of methyl methacrylate were used instead of 100% by mass of t-butyl methacrylate to extract methacrylic acid. The extraction efficiency for MAA and the concentration of the extraction solvent in water phase were measured in the same manner as in Example 1. The results are shown in Table 3.

TABLE 3

| | Comp. Ex. 1 | Comp. Ex. 2 | Comp. Ex. 3 |
| --- | --- | --- | --- |
| Extraction solvent | Heptane | MAL | Heptane + MMA (Heptane of 66.6% by mass) |

TABLE 3-continued

| | | Comp. Ex. 1 | Comp. Ex. 2 | Comp. Ex. 3 |
|---|---|---|---|---|
| Amount charged at the time of extraction | Aqueous MAA solution (g) | 70.00 | 70.02 | 70.06 |
| | Extraction solvent (g) | 30.03 | 30.21 | 30.04 |
| Extraction efficiency for MAA (%) | | 65.9 | 90.8 | 75.4 |
| Concentration of extraction solvent in water phase (%) | | 0.0 | 4.1 | 0.6 |

In Table 3, MMA represents methyl methacrylate and MAL represents methacrolein, respectively.

The extraction efficiency for MAA was high in the case of Examples 1 and 2, in each of which the extraction solvent containing t-butyl methacrylate was used. Further, the amount of t-butyl methacrylate transferred to water phase was small in both cases. Consequently, methacrylic acid can be extracted in high efficiency and at low cost according to the methods of Examples 1 and 2.

On the other hand, in the case of Comparative Examples 1 in which the extraction solvent composed of heptane was used, the extraction efficiency for MAA was low.

In the case of Comparative Examples 2 in which the extraction solvent composed of methacrolein was used, the amount of methacrolein transferred to water phase was large, and it took much time to recover methacrolein from the water phase, and hence, this was unecomonical.

In the case of Comparative Examples 3 in which the extraction solvent composed of heptane and methyl methacrylate was used, the extraction efficiency for MAA was low.

What is claimed is:

1. A method for extracting methacrylic acid, comprising the steps of:
    (a) adding an extraction solvent comprising t-butyl methacrylate to a methacrylic acid aqueous solution; and
    (b) causing methacrylic acid to transfer to the extraction solvent.

2. The method for extracting methacrylic acid according to claim 1, wherein the extraction solvent is a mixture of t-butyl methacrylate and methyl methacrylate.

3. The method for extracting methacrylic acid according to claim 1, wherein the amount of the extraction solvent to be used is in the range of 0.5 to 15 times with respect to the total mass of the methacrylic acid aqueous solution.

4. The method for extracting methacrylic acid according to claim 2, wherein a mass fraction of methyl methacrylate in the extraction solvent is in the range of 3 to 90%.

* * * * *